United States Patent [19]

Kee et al.

[11] Patent Number: 5,738,091
[45] Date of Patent: *Apr. 14, 1998

[54] SUCTION CATHETER CONNECTION ARRANGEMENTS WITH AUTOMATICALLY OPERATED VALVE

[75] Inventors: Kok-Hiong Kee; James G. Schneider; Neal G. Koller, all of St. Louis, Mo.; Robert H. Bruno, Avon, Conn.

[73] Assignee: Sherwood Medical Company, St. Louis, Mo.

[*] Notice: The term of this patent shall not extend beyond the expiration date of Pat. No. 5,343,857.

[21] Appl. No.: 479,239

[22] Filed: Jun. 7, 1995

Related U.S. Application Data

[60] Continuation of Ser. No. 161,001, Dec. 3, 1993, abandoned, which is a division of Ser. No. 962,756, Oct. 19, 1992, Pat. No. 5,309,902.

[51] Int. Cl.$^6$ .............. A62B 7/10; A62B 9/04; A61M 16/00; A61M 5/00
[52] U.S. Cl. .............. 128/205.12; 128/202.27; 128/207.14; 128/207.16; 128/912; 128/204.18; 128/205.24; 128/908; 604/171; 604/247; 604/119
[58] Field of Search .............. 128/202.27, 200.23, 128/203.12, 200.22, 205.13, DIG. 26, 911, 912, 908, 204.18, 207.14, 207.16, 205.12, 205.24; 604/171, 172, 247, 167, 169, 119, 163, 256, 100, 117; 285/330, 331, 332, 332.1

[56] References Cited

U.S. PATENT DOCUMENTS

| | | | |
|---|---|---|---|
| 2,946,156 | 7/1960 | Bailey | 49/81 |
| 2,956,819 | 10/1960 | Sies | 285/93 |
| 3,112,748 | 12/1963 | Colburn | 128/350 |
| 3,517,669 | 6/1970 | Buono et al. | 128/276 |
| 3,526,249 | 9/1970 | Baustian | 137/614.11 |
| 3,577,992 | 5/1971 | Merry et al. | 128/349 |
| 3,991,762 | 11/1976 | Radford | 128/207.14 |
| 4,240,417 | 12/1980 | Holever | 128/203.12 |
| 4,246,899 | 1/1981 | Loseff | 128/276 |
| 4,351,328 | 9/1982 | Bodai | 128/202 |
| 4,356,823 | 11/1982 | Jackson | 128/276 |
| 4,468,224 | 8/1984 | Enzmann et al. | 604/247 |
| 4,510,933 | 4/1985 | Wendt et al. | 128/207.14 |
| 4,638,539 | 1/1987 | Palmer | 29/157 |
| 4,736,732 | 4/1988 | Shimonaka et al. | 128/4 |

(List continued on next page.)

FOREIGN PATENT DOCUMENTS

| | | | |
|---|---|---|---|
| 0 414 997 | 4/1990 | European Pat. Off. | |
| 3042229 | 5/1982 | Germany | 604/167 |
| 2 207 736 | 2/1989 | United Kingdom | |

*Primary Examiner*—Kimberly L. Asher
*Attorney, Agent, or Firm*—Montgomery W. Smith; Ari M. Bai

[57] ABSTRACT

The invention relates to a suction catheter device usable with a respiratory support system which includes a catheter enveloped in a sleeve having a proximal end connector for connection to a suction source through a suction control device such as a suction control valve, and a distal end connector for attachment to a manifold of the respiratory support system. The proximal end connector includes a normally closed valve therein which prevents air flow through the catheter until a suction control device is attached thereto. The proximal end connector may also be adapted for use on a dual lumen catheter and thereby include a fluid injection passage having a one-way check valve therein. The distal end connector of the suction catheter device includes a magnifying window through which a portion of the catheter within the connector can be viewed. The catheter includes one or more markings thereon which indicate the relative position of the catheter and the connector, and which can be viewed through the magnifying window of the connector to indicate to the medical worker how far the catheter has been inserted into the patient's trachea or lungs. The invention also includes the method of assembly of the suction catheter device and the method of use thereof in conjunction with the respiratory support system.

23 Claims, 6 Drawing Sheets

U.S. PATENT DOCUMENTS

| | | | |
|---|---|---|---|
| 4,751,924 | 6/1988 | Hammerschmidt et al. | 128/207.15 |
| 4,762,125 | 8/1988 | Leiman et al. | 128/207.15 |
| 4,796,615 | 1/1989 | Bullock et al. | 128/202.27 |
| 4,805,611 | 2/1989 | Hodgkins | 128/207.14 |
| 4,832,696 | 5/1989 | Luther et al. | 604/164 |
| 4,834,710 | 5/1989 | Fleck | 604/171 |
| 4,838,255 | 6/1989 | Lambert | 128/202.16 |
| 4,850,350 | 7/1989 | Jackson | 128/207.16 |
| 4,979,765 | 12/1990 | Bartholomew | 285/93 |
| 5,025,806 | 6/1991 | Palmer et al. | 128/203.12 |
| 5,029,580 | 7/1991 | Radford et al. | 128/207.14 |
| 5,083,561 | 1/1992 | Russo | 128/207.16 |
| 5,088,486 | 2/1992 | Jinotti | 128/207.14 |
| 5,125,893 | 6/1992 | Dryden | 604/54 |
| 5,134,996 | 8/1992 | Bell | 128/207.14 |
| 5,139,018 | 8/1992 | Brodsky et al. | 128/207.14 |
| 5,215,522 | 6/1993 | Page et al. | 604/33 |
| 5,220,916 | 6/1993 | Russo | 128/207.16 |
| 5,234,411 | 8/1993 | Vaillancourt | 604/171 |
| 5,261,416 | 11/1993 | Taussig | 128/759 |
| 5,309,902 | 5/1994 | Kee et al. | 128/202.27 |
| 5,333,607 | 8/1994 | Kee et al. | 128/202.27 |
| 5,343,857 | 9/1994 | Schneider et al. | 128/202.27 |

SUCTION CATHETER CONNECTION ARRANGEMENTS WITH AUTOMATICALLY OPERATED VALVE

This is a continuation of application(s) Ser. No. 08/161, 001 filed on Dec. 3, 1993, now abandoned, which is a division of Ser. No. 07/962,756 filed on Oct. 19, 1992, now U.S. Pat. No. 5,309,902.

BACKGROUND OF THE INVENTION

1. Field of the Invention

This invention relates generally to apparatus used in conjunction with a respiratory support system. More specifically, the present invention relates to a method and apparatus for using a suction catheter device as part of a respiratory support system. Even more specifically, the present invention relates to the attachment and detachment of a suction catheter device from a suction control valve and a ventilator manifold of a respiratory support system without interruption or loss of continuous respiratory support of a patient.

2. Prior Art

Respiratory support systems used for the ventilation of critically ill patients are now commonly used in medical facilities. Typically, a prior art respiratory support system includes a tracheal tube, positioned either directly or through the nose or mouth into the trachea of a patient, a manifold connected to the tracheal tube at one port position thereof, and a source of breathable gas connected at a second port thereof. The purpose of the respiratory support system is to assist the patient in maintaining adequate blood oxygenation levels without overtaxing the patient's heart and lungs.

While a patient is attached to the respiratory support system, it is periodically necessary to aspirate fluid from the patient's trachea or lungs. In the past, in order to accomplish aspiration, it has been necessary to disassemble part of the respiratory support system, either by removing the ventilator manifold or by opening a port thereof and inserting a small diameter suction tube down the tracheal tube and into the patient's trachea and lungs. The fluid was then suctioned from the patient and the suction catheter was removed and the respiratory support system reassembled. However, due to the interruption of respiratory support during this procedure, a patient's blood oxygen often dropped to an unacceptably low level, even when other previously known breathing assistance efforts were simultaneously provided.

One solution to the above problem, which is generally exemplary of the prior art, is shown in U.S. Pat. No. 5,073,164 to Hollister et al., which includes a ventilator manifold having an access port therethrough which is adapted to receive a connector of the suction catheter device. The suction catheter device positions a catheter within the ventilator manifold without substantial manifold pressure loss. The suction catheter device includes an envelope which is positioned around the catheter portion thereof in order to prevent contamination of catheter surfaces intended to be inserted into the patient's trachea and lungs.

Although this type of ventilator manifold and suction catheter device connection allows continuous respiratory support of the patient during suctioning of fluid from the patient's trachea and lungs, it nevertheless has several drawbacks associated with its use. For example, removal of the suction catheter device from the manifold, such as for the purpose of replacing the suction catheter device, or for attaching another accessory to the manifold (e.g., a manual resuscitation bag or a metered dose inhaler) cannot be accomplished without loss of internal manifold pressure and thereby a compromise of the integrity of the respiratory system. Further, separation of the Hollister et al. suction catheter device from their suction control valve cannot be accomplished without opening the manifold to atmospheric pressure through the catheter. Therefore, replacement of either the suction catheter device or the suction control valve is not possible without loss of internal manifold pressure. Instead, respiratory support of the patient is compromised whenever the suction catheter device or the suction control valve is removed from the system for any reason. Since the suction catheter device tends to become contaminated relatively quickly with respect to the suction control valve and the ventilator manifold, it must be changed out of the system and replaced on a relatively frequent basis. However, because of the problems caused by loss of respiratory support during replacement, the ventilator manifold and/or the suction control valve are often prematurely discarded along with the suction catheter device in order to limit replacement time and the number of replacement procedures required.

U.S. Pat. No. 4,351,328 to Bodai attempts to solve one of the above problems by forming an opening in the ventilator manifold which is blocked by a pre-punctured resilient seal through which a catheter can be passed without substantially affecting the integrity of the system, i.e., without substantial gas exchange or pressure loss between the interior of the manifold and the atmosphere. The Bodai device, although allowing entry and removal of a suction catheter through the ventilator manifold during continuous respiratory support of a patient, nevertheless fails to completely resolve the existing problems in the prior art. Specifically, the pre-punctured resilient material in Bodai's manifold opening allows only for the insertion of a catheter therethrough, and fails to accommodate a suction catheter device which includes a collapsible envelope which surrounds and seals the catheter against exterior surface contamination. Further, there is no design consideration for the attachment of other accessory devices to the manifold, such as a manual resuscitation bag or a metered dose inhaler, which are often necessary for use in the care of a patient.

Also, the system described by Bodai tends to cause mucus and other fluids from the patient's lungs and trachea to collect in the manifold as the catheter is pulled past the pre-punctured resilient seal when being withdrawn. Because of this contamination problem, it is often necessary to replace the manifold on a more frequent basis than would otherwise be necessary, which necessitates a pressure breach in the support system.

There therefore exists a need in the art for a respiratory support system which includes a ventilator manifold which allows simple attachment and detachment of a suction catheter device therefrom during continuous patient respiratory support, without substantial pressure loss from the manifold and without substantial collection of body fluids in the manifold. There also exists a need in the art for a suction catheter device and a suction control valve which can be disassembled and reassembled, individually or collectively, from the respiratory support system during use thereof, and reassembled or replaced thereafter, without causing interior pressure loss from the ventilator manifold.

OBJECTS AND SUMMARY OF THE INVENTION

A principle object of the present invention is to provide a respiratory support system which allows attachment thereto and detachment therefrom of a suction catheter device without interruption of continuous patient respiratory support.

A further object of the present invention is to provide a suction catheter device which is designed to be capable of interchangeably engaging and disengaging a normally closed valve of a manifold port of a respiratory support system at one end thereof, and a suction control valve at the other end thereof, without comprising internal manifold pressure integrity.

Another object of the present invention is to provide a suction catheter device which is capable of being disassembled from the respiratory support system to allow replacement of a suction catheter device or a component part of the respiratory support system, such as the suction control valve thereof, during respiratory support of a patient without compromising the integrity of the ventilator manifold.

A further object of the present invention is to provide a suction catheter device which is designed to be capable of engaging a ventilator manifold at one end thereof and allowing engagement and disengagement of a suction control valve at an opposite end thereof without compromising internal pressure integrity of the ventilator manifold.

It is also an object of the present invention to provide a respiratory support system having a manifold and a suction control valve, and a suction catheter device usable therewith, which may include "time-in-use" indicators on one or more of the component parts of the respiratory support system or the suction catheter device which indicate the amount of time each component has been a part of the overall respiratory support system and which may also indicate preferred or recommended time periods for replacement of each individual component.

These and other objects of the present invention are realized in a presently preferred embodiment thereof, described by way of example and not necessarily by way of limitation, which provides for interchangeable use of components of a respiratory support system and a suction catheter device during respiratory support of a patient, without comprising the integrity of the respiratory support system through loss of internal pressure in the manifold thereof. A ventilator manifold formed with an accessory device access port which includes a normally closed valve therein is intended to be part of the respiratory support system. The valve maintains the pressure differential between the atmosphere and the interior of the ventilator manifold regardless of interior manifold pressure fluctuations. The invention includes a suction catheter device which includes a manifold-end connector having an adaptor formed to fit within the accessory device access port of the manifold and to sealingly engage therewith. Positioning the adaptor into the access port of the manifold forces a normally closed valve therein to an open position. The access port and adaptor may include a detent and stop-type locking arrangement for locking the adaptor within the port against inadvertent withdrawal thereof during use, and for orienting the adaptor in a single unique position relative to the access port to align a passageway through the side of the access port with an opening through the side of the adaptor which allows cleaning and/or lavage fluid to be injected into the interior of the adaptor and/or the interior of the manifold if desired.

The manifold-end connector allows the catheter to pass freely therethrough and includes a window having a magnifying lens therein which allows a user to view a portion of the catheter within the adaptor in a magnified size. The catheter itself may also include positioning marks thereon which, when viewed through the lens of the connector, inform the user of the position of the distal tip of the catheter relative to the connector so that the user can readily determine how far the catheter has been inserted into the patient's trachea or lungs, or conversely, how far the catheter has been withdrawn through the connector.

The suction catheter device also includes a valve-end connector which is designed to allow snap-in connection of an insert within the connector housing which will properly position both the end of the suction catheter and the catheter sleeve within the connector. The connector includes a septum which closes the end of the catheter against fluid flow therethrough until the suction control valve of the respiratory support system is properly attached to the connector to force the septum open and allow fluid flow between the catheter and the suction control valve.

Alternatively, the suction catheter device may include a dual-lumen catheter for suction and irrigation purposes, and the valve-end connector therefore can include a one-way saline injection port attached in fluid flow connection with the fluid injection lumen of the dual-lumen catheter.

DETAILED DESCRIPTION OF THE PREFERRED EMBODIMENTS

As shown in the exemplary drawings for the purposes of illustration, an embodiment of a manifold and suction control valve of a respiratory support system attached to a suction catheter device made in accordance with the principles of the present invention, referred to generally by the reference numeral 10, is provided for interchangeable use as part of the respiratory support system without interruption of respiratory support of the patient.

Figure 1:
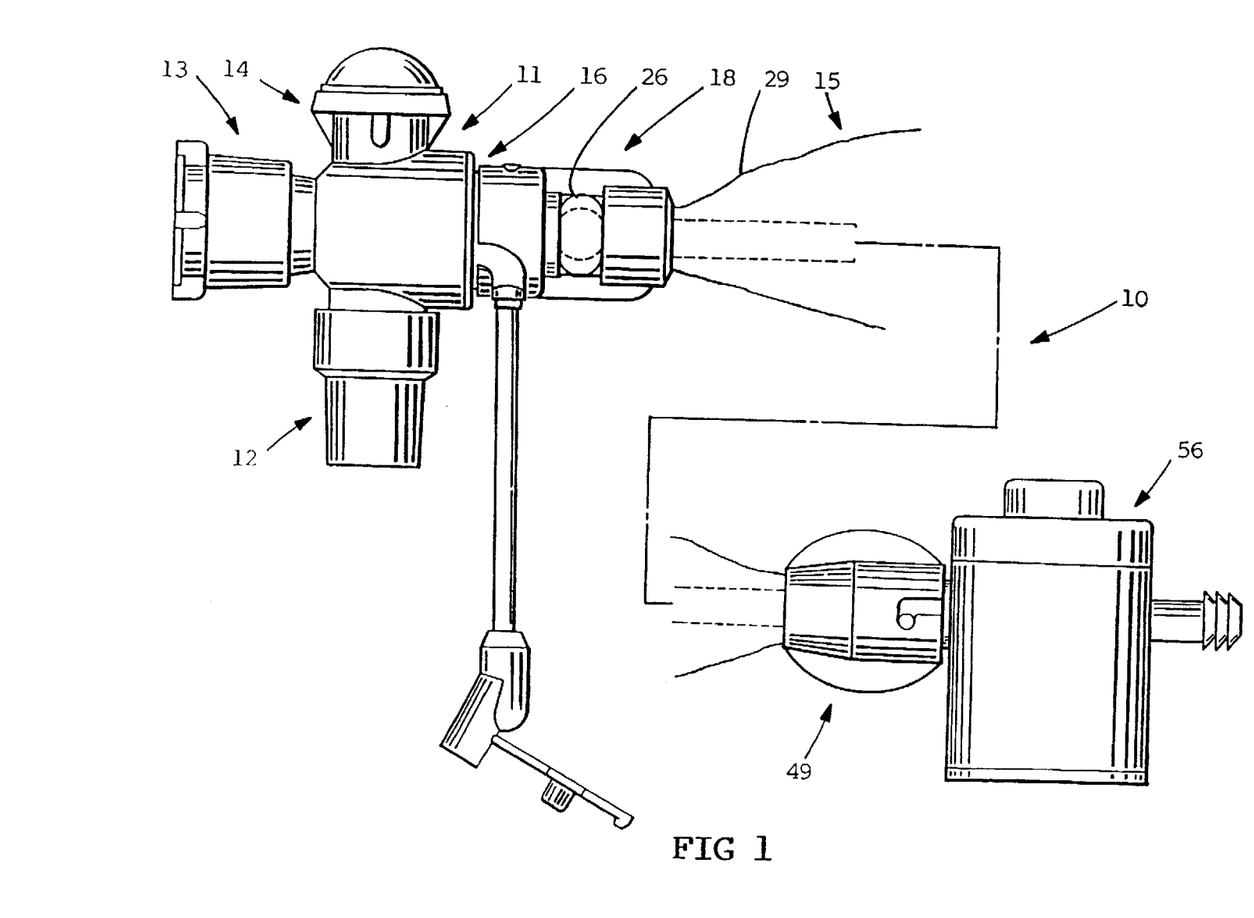
FIG. 1 shows a suction control valve and a manifold of a respiratory support system attached for use to a suction catheter device formed in accordance with the principles of the present invention.

More specifically, as shown in FIG. 1, the ventilator manifold 11 includes a plurality of access ports which facilitate its connection to a ventilator circuit of the respiratory support system and to the patient. The manifold 11 is attached to a patient for fluid flow communication with the patient's lungs by the connection of the patient attachment port 13 thereof to the connector of an endotracheal tube assembly (not shown) which has been previously positioned in the trachea of a patient by any one of several well known procedures.

Ventilator circuit connection port 12 of the manifold 11 is designed for connection to flexible breathing hoses from the ventilator (not shown) in a well-known manner, such as through a "Y" site connector. Port 14 is normally capped and closed against air flow except for instances when nonpressurized ventilation is desired. The ventilator circuit provides a breathable gas mixture to the patient through one hose, and receives expelled air from the patient's lungs through another hose. The ventilator circuit further commonly includes various valves, regulators, and the like associated with the hoses in order to effect respiration of the patient. The manifold 11, and hoses attached thereto at the ventilator circuit connection port 12, are generally made of disposable plastic material and are generally intended to be used by only one patient and then discarded.

When attached to the patient, the entire respiratory support system is designed to isolate the patient's lungs from the atmosphere and allow pressurized forced ventilation of a gas mixture of a high oxygen content from the ventilator into the patient's lungs. Commonly ventilators of this type are used to maintain a positive end expiratory pressure (PEEP) within the ventilator manifold 11 and the patient's lungs at all times during exhalation. This technique is commonly used because of the benefit of supplying a minimum concentration of oxygen to the patient at all times for maintaining a proper blood oxygenation level. The PEEP procedure also keeps a large number of lung alveoli of the patient open at all times during respiratory support, thus increasing the effective lung area subject to ventilation.

Prevailing respiratory support techniques including PEEP, have made it very disadvantageous to interrupt respiratory support to the patient by opening the ventilator manifold to the atmosphere and thereby causing a loss of interior manifold pressure. The attachment of accessory devices thereto for necessary medical procedures has had to be avoided therefrom because of the loss of isolation of the respiratory system from the atmosphere during these procedures, and the immediate loss of effective lung surface area due to collapse of the patient's lung alveoli. Further, when such procedures have been prolonged for any reason, the patient's blood oxygen has often dropped to inadequate levels, and subsequently forced overexertion of the patient's lungs and heart in order to return the blood oxygen level to normal. Also, disassembly and reassembly of the respiratory support system components for procedures with prior art accessory devices often becomes very time consuming for the medical worker involved.

The present invention resolves the problems associated with loss of isolation of the respiratory support system from the atmosphere when accessory devices must be inserted or attached in order to perform necessary medical procedures, or alternatively, when they must be replaced, during respiratory support of a patient.

Specifically, the manifold 11 of the present invention includes an accessory device access port 16 which is in fluid flow communication with the interior of the manifold 11. The access port 16 includes a normally closed valve 17 preferably made of a resilient material such as rubber or silicone (see FIG. 4) which maintains the interior of the manifold 11 isolated from the atmosphere at all times. As explained above, the interior of the manifold 11, although experiencing constant pressure fluctuations, is generally kept at a pressure which is slightly above atmospheric pressure in order to properly administer oxygen according to the PEEP procedure. Further, details of the ventilator manifold 11 and the accessory access port 16 thereof can be found in applicant's co-pending U.S. applications, Ser. No. 07/962, 755, filed Oct. 19, 1992, and Ser. No. 07/962,755, filed Oct. 19, 1992, which are both incorporated herein by reference.

Figure 2:
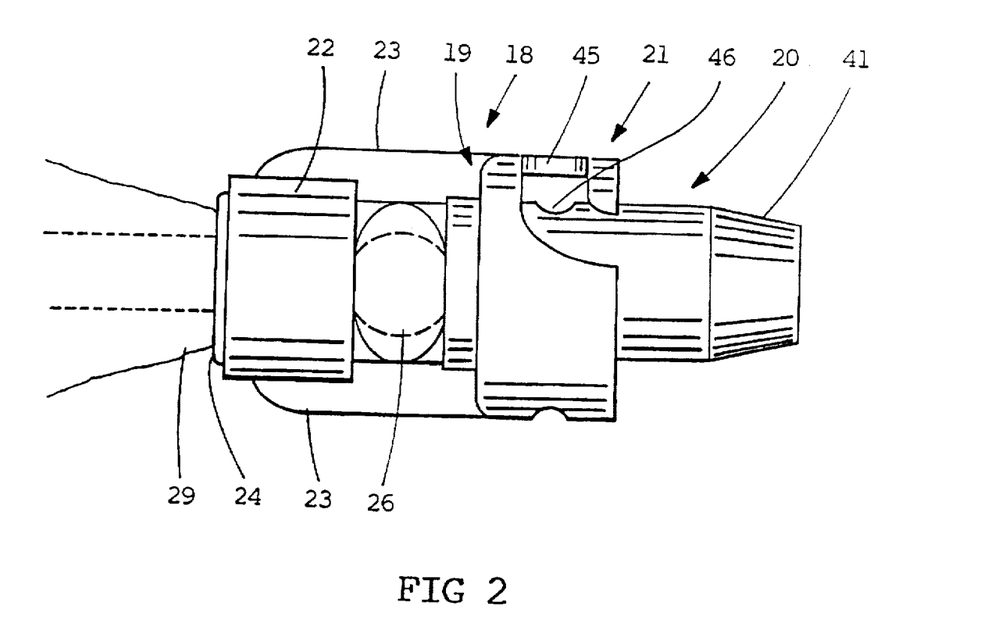
FIG. 2 is a plan view of a portion of the suction catheter device which includes the manifold-end connector thereof formed in accordance with the principles of the present invention.
Figure 3:
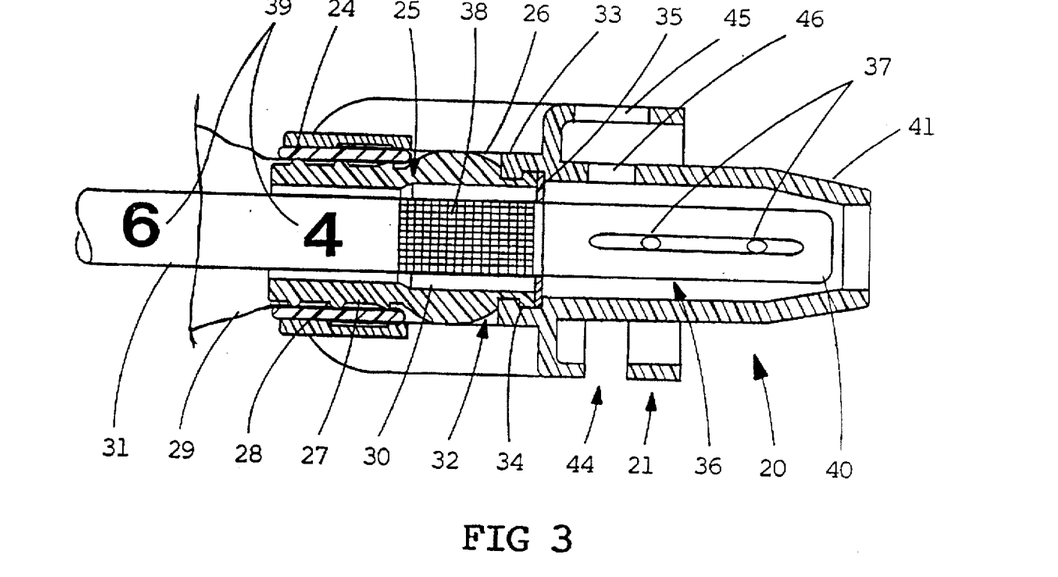
FIG. 3 is a cross-sectional view of the manifold-end connector of the suction catheter device shown in FIG. 2.

Referring now to FIGS. 2 and 3, the manifold-end connector 18 of the suction catheter device 15 is shown. The connector 18 includes a unitary housing 19 which forms an adaptor 20, a locking mechanism 21, a base ring 22, and a plurality of rib members 23. The base ring 22 forms a generally cylindrical opening through which the sleeve attachment ring 24 can be inserted for frictional engagement to hold the sleeve 29 in proper position relative to the connector 18.

A magnifying insert 25 is formed as a generally cylindrical member having a bulbous lens 26 at one end thereof formed of clear plastic and a cylindrical extension 27 formed at the other end thereof. The cylindrical extension 27 is formed to a slightly smaller diameter than the sleeve attachment ring 24 and may include ribbing 28 around the exterior surface thereof to aid in frictional engagement between the extension 27 and the sleeve attachment ring 24. When constructed for use, the sleeve 29 is positioned around the sleeve attachment ring 24 so as to be frictionally engaged between the extension 27 and the interior surface of the sleeve attachment ring 24, and wrapped around at least a portion of the exterior surface of the sleeve attachment ring 24 to also become frictionally engaged with the base ring 22 when the sleeve attachment ring 24 is inserted therein.

The lens 26 of the magnifying insert 25 is preferably formed of a substantially clear plastic which magnifies the portion of the catheter 31 for viewing by a user through the generally cylindrical opening or window 32 formed by the unitary housing 19 between the base ring 22 and the locking mechanism 21. The window 32 extends around the entire circumference of the unitary housing 19 and allows viewing of the lens 26 by a user at any viewing angle except where the window 32 may be slightly covered by a portion of the ribbed members 23 which extend between the base ring 22 and the locking mechanism 21.

The unitary housing 19 also includes an annular locking shoulder 33 which operates in conjunction with an annular locking shoulder 34 on the magnifying insert 25 to secure the magnifying insert 25 in proper position within the unitary housing 19, and to ensure an air-tight seal therebetween and with the sealing ring 35.

The magnifying insert 25 has a generally cylindrical passageway 30 formed therethrough which is of slightly larger diameter than the catheter 31 and which allows uninhibited movement of the catheter 31 therethrough.

If desired, the catheter 31 may be formed with a tip 36 of softer material than the remainder of the catheter 31 and which may include side openings 37 therein. The catheter 31 may also include a series of markings such as ring marking 38 and/or number markings 39 along the length thereof which will tend to be magnified when located beneath the lens 26. The marking 38 is intended to indicate the completely withdrawn position of the catheter 31 into the adaptor 20. For example, in operation, the user can withdraw the catheter 31 through the connector 18 until the ring marking 38 moves into view within the lens 26. Positioning of the ring marking 38 beneath the lens 26 indicates to the user that the catheter 31 has been withdrawn the entire recommended distance through the connector 18 and cannot be further withdrawn without risking inadvertent passage of the side openings 37 of the catheter 31 past the sealing ring 35, which would effectively allow leakage of air past the sealing ring 35. As is readily evident, an even greater leakage of air would occur if withdrawal of the catheter 31 continued until the distal end 40 thereof passed through the sealing ring 35 or through the connector 18 entirely.

The number markings 39 may be positioned along the catheter 31 so as to indicate to the user a particular predetermined distance which the distal end 40 thereof extends beyond the connector 18. As each number marking 39 appears in the lens 26, the user can recognize the number as corresponding to a particular predetermined distance that the distal end 40 is extending beyond the connector 18. In this manner, when the connector 18 is attached to a manifold 11 of a respiratory support system, the user can readily determine how far down a patient's trachea or lungs the catheter 31 has been inserted during an aspiration procedure by noting the particular number marking 39 visible through the lens 26.

Figure 4:
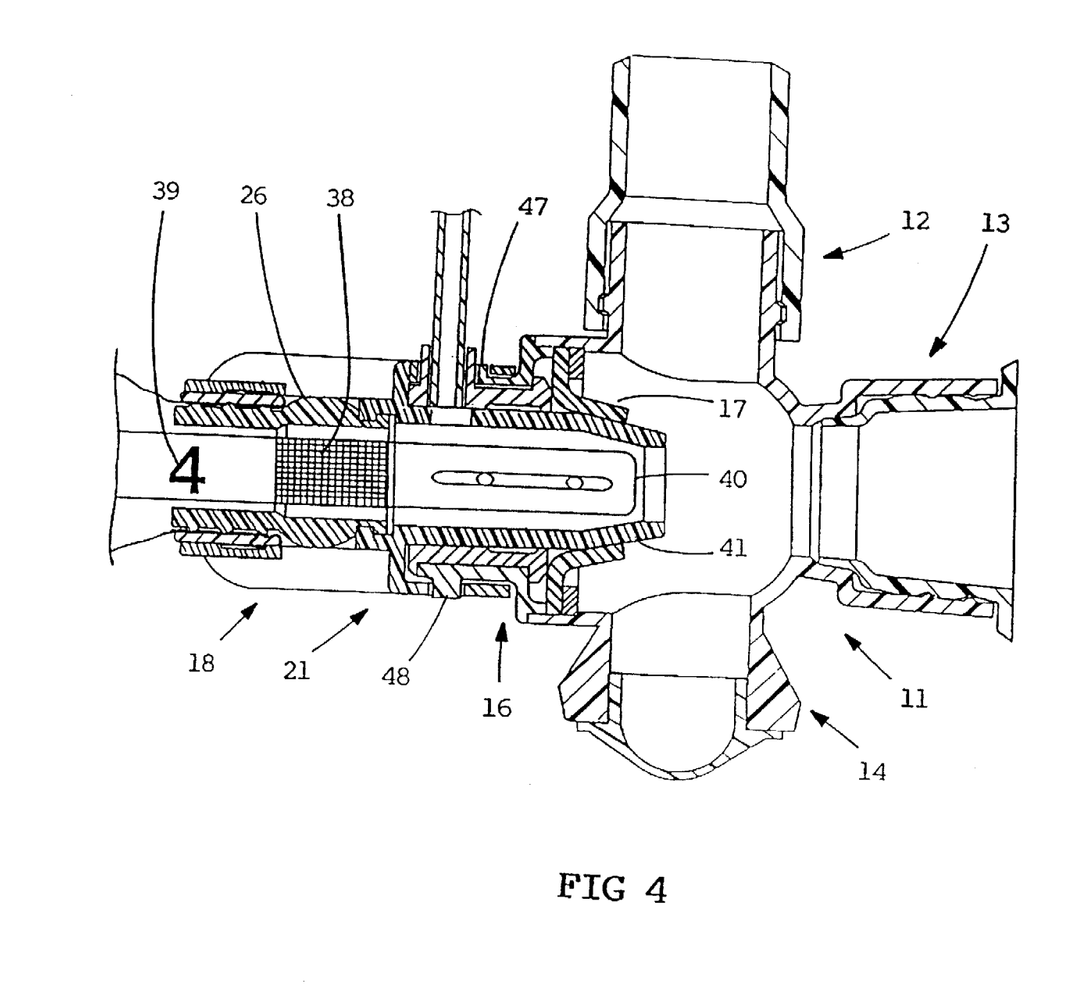
FIG. 4 shows a partial cutaway view of the ventilator manifold, with the manifold-end connector of the suction catheter device attached to the accessory device access port thereof being shown in cross-section.

The adapter 20 and locking mechanism 21 of the connector 18 operate to attach the connector 18 to the ventilator manifold 11. As best shown in FIG. 4, attachment of the connector 18 to the manifold 11 is effected by insertion of the adapter 20 into the access port 16 until the tapered top section 41 thereof engages the valve 17 and forces it toward the interior of the manifold 11. Upon complete insertion of the adapter 20 into the access port 16, the valve 17 is completely open.

The locking mechanism 21 of the connector 18 is formed to encircle a portion of the adapter 20 and includes a pair of arcuate slots 44 and 45 which operate together to ensure secure attachment of the connector 18 to the access port 16 of the manifold 11, and also ensure proper relative orientation between the adapter 20 and the access port 16, to cause the injection fluid opening 46 of the adapter 20 to be positioned in alignment with the side opening 47 of the access port 16 when the adapter 20 is properly locked in position therein for use. The arcuate slot 44 is sized to be engageable with the nub 48 which is located directly opposite the side opening 47 on the access port 16. The arcuate slot 45 is larger in width than the arcuate slot 44 and therefore can accommodate the side opening 47 of the access port 16. As is readily evident, the adapter 20 can only be locked in position within the access port 16 in one unique relative orientation in which the injection fluid opening 46 and the side opening 47 are in alignment.

A more detailed description of the access port 16 of the manifold 11 and its attachment to the adapter 20 and locking mechanism 21 of the connector 18 is presented in applicant's co-pending U.S. application Ser. No. 07/962,755, filed Oct. 19, 1992, which incorporated herein by reference.

Figure 5:
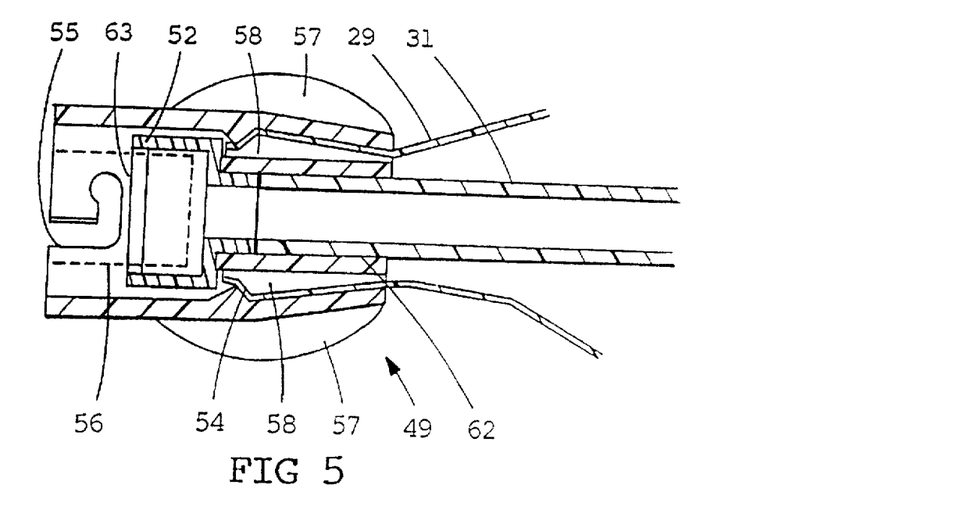
FIG. 5 is a cross-sectional view of the valve-end connector of the suction catheter device formed in accordance with the principles of the present invention.
Figure 6:
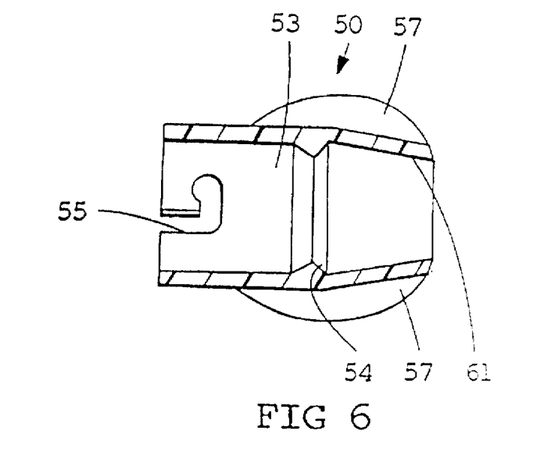
FIG. 6 is a cross-sectional view of the housing portion of the valve-end connector.
Figure 7:
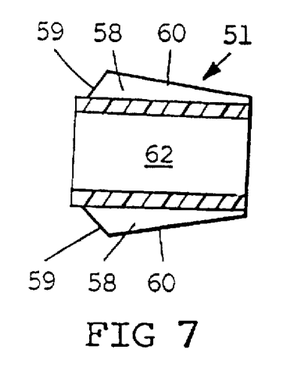
FIG. 7 is a cross-sectional view of the insert portion of the valve-end connector.

Referring now to FIGS. 5–7, the valve-end connector 49 of the suction catheter device 15 is shown. The connector 49 includes three main components including a housing 50, a snap-in insert 51, and a slit septum 52. The housing 50 forms a passageway 53 therethrough which has an annular shoulder 54 protruding thereinto at an approximately centrally located position along the passageway 53. The housing 50 also includes a pair of locking slots 55 for attachment of the connector 49 to the suction control valve 56 (shown in dashed lines in FIG. 5) and a pair of longitudinally oriented finger grips 57 which facilitate rotation of the connector 49 for attachment the suction control valve 56.

The snap-in insert 51 is a generally cylindrical tubular member having a plurality of uniformly spaced fins 58 positioned longitudinally therealong in a plurality of uniformly spaced locations. Each fin 58 includes a locking shoulder 59 at one end thereof and a tapered edge 60 along the length thereof. The locking shoulder 59 and tapered edge 60 are sized to match the annular shoulder 54 and the tapered portion 61 of the housing passageway 53 so as to securely hold the catheter sleeve 29 in a friction fit within the housing 50 between the fins 58 and the tapered portion 61 of the passageway 53.

The snap-in insert 51 also forms a tubular channel 62 therein which is sized to accommodate the proximal end of the catheter 31 and the distal end of the slit septum 52 in a permanently attached manner such as by solvent bonding or the like. The slit 63 in the septum may be of any desired shape or configuration such a linear, curvelinear, cross, or the like, which can be easily pushed open by the suction control valve 56 and which will return to its closed position upon its removal.

It should be noted that the connector 49 intentionally forms an open air flow path from the interior of the sleeve 29 past he snap-in insert 51. Air can pass between the fins 58 and around the slitted septum 52 to the atmosphere. This air flow path is intentionally designed to ensure that the sleeve 29 is not sealed against air flow between the interior thereof and the atmosphere. This prevents pressure or vacuum build up within the sleeve 29 during operation of the suction catheter device 15 due to contraction and expansion of the sleeve 29 caused by the movement of the catheter 31 through the respiratory manifold 11.

Figure 8:
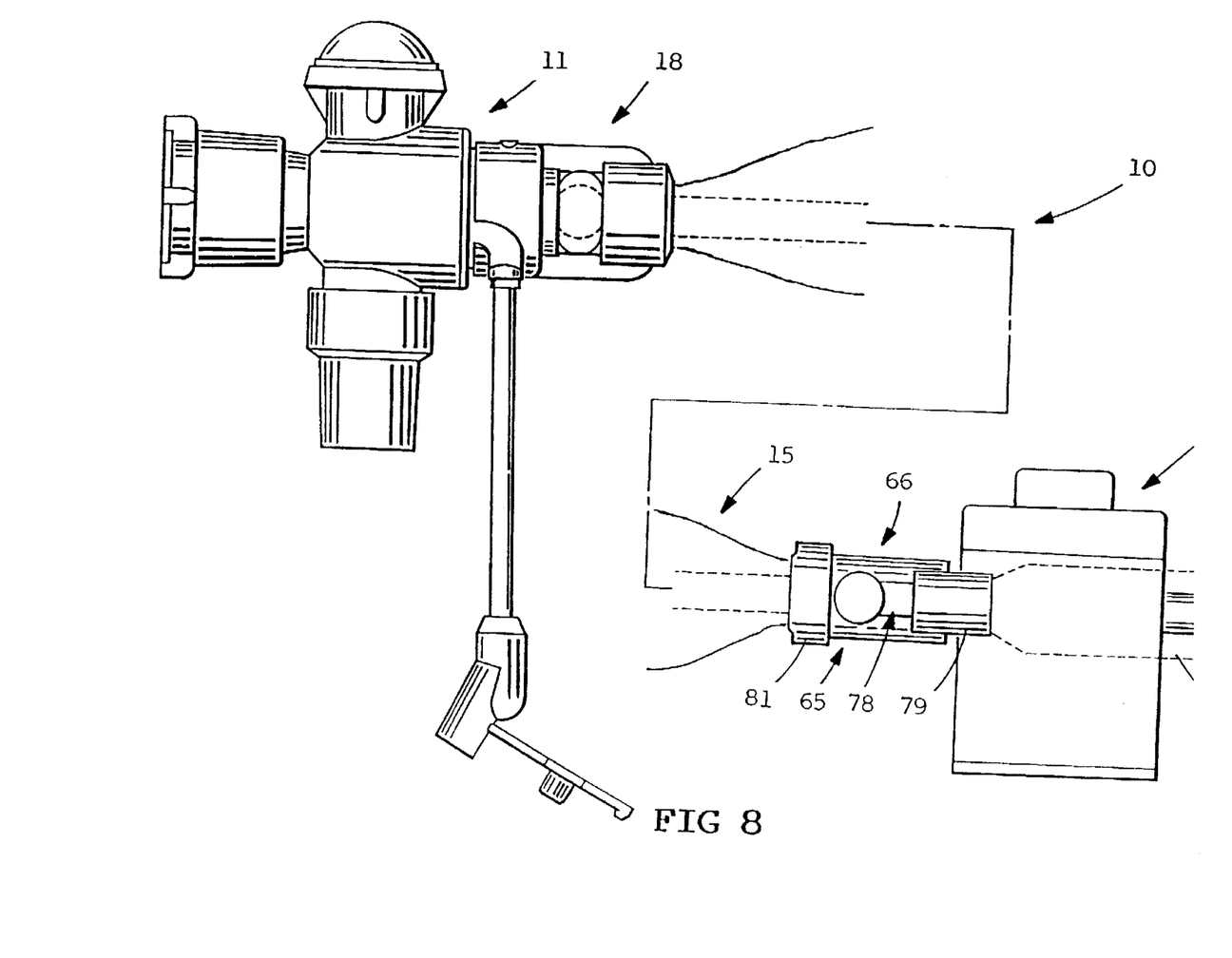
FIG. 8 is a plan view of an alternative embodiment of the suction catheter device formed in accordance with the principles of the present invention.

Referring now to FIG. 8, an alternative embodiment of the suction catheter device 15 is shown which is substantially identical to the suction catheter device 15 described above, except that the catheter thereof is a dual-lumen catheter and the valve-end connector is modified to allow injection of fluid from a flexible fluid vial 64 through the second lumen.

Figure 9:
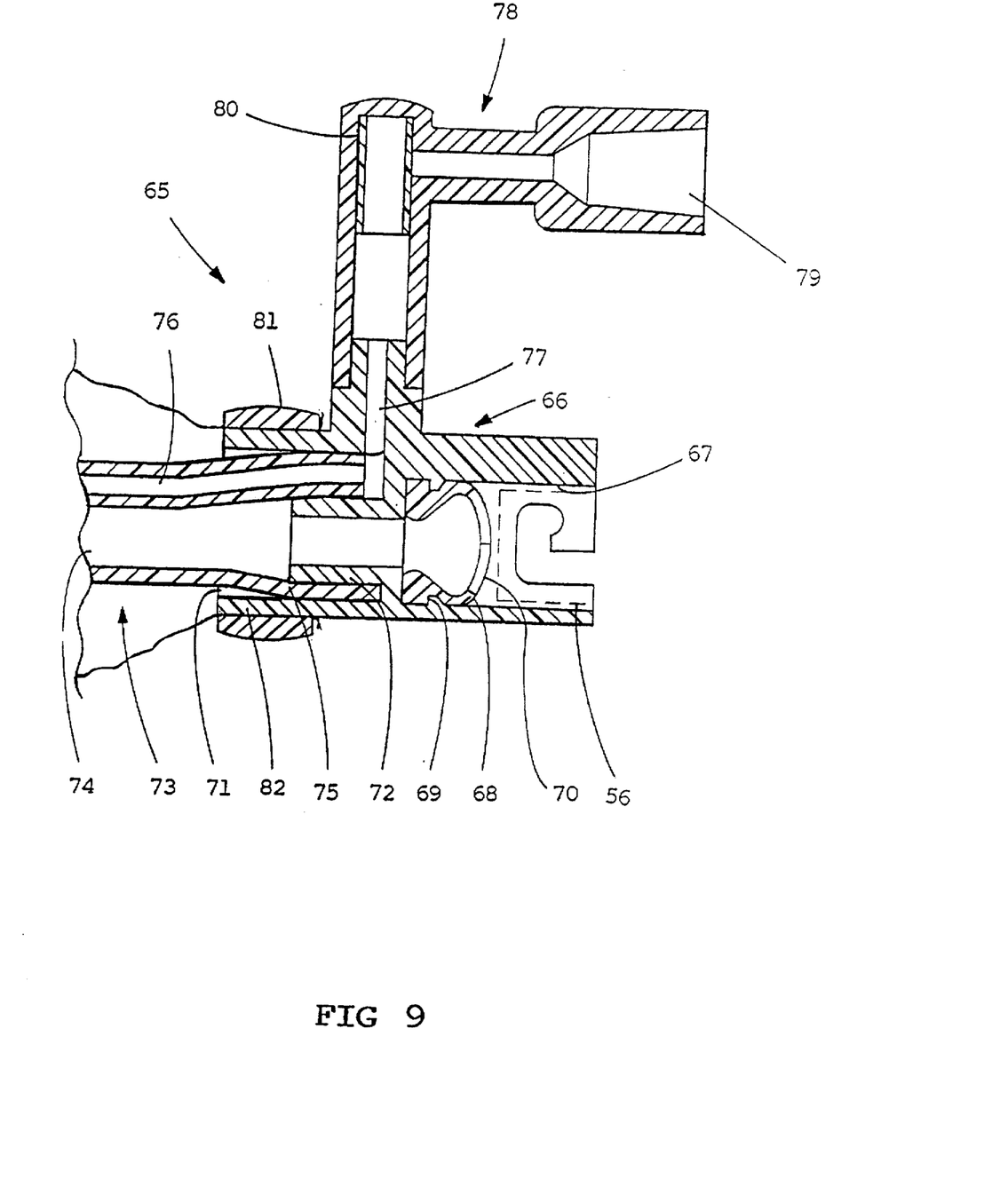
FIG. 9 is a cross-sectional view of the valve-end connector of the alternative embodiment of the suction catheter device shown in FIG. 8.

More specifically, as shown in FIG. 9, the dual-lumen valve-end connector 65 includes a housing 66 which forms a generally cylindrical opening 67 into which the suction control valve 15 (shown in dashed lines) can be inserted for connection, and in which a slitted septum 68 is affixed such as by annular shoulder 69. The slitted septum 68 includes a normally closed slit 70 therein which is opened by the insertion of the suction control valve in the manner described previously with respect to the single-lumen valve-end connector 49 above.

The housing 66 also includes a second cylindrical opening 71 which has a tubular extension 72 formed therein. The opening 71 is sized to receive the proximal end of the dual-lumen catheter 73, and the tubular extension 72 is designed to be inserted within the larger (suction) lumen 74 of the proximal end 75 of the dual-lumen catheter 73.

As is evident in FIG. 9, the proximal end 75 of the dual-lumen catheter 73 is somewhat larger in diameter than the remainder of the catheter 73. This is preferably due to intentional manufacturing of the catheter 73 with an enlarged proximal end 75, and not necessarily due only to stretching of the proximal end 75 about the tubular extension 72. This is a desirable feature of the present invention in that intentional over-sizing of the proximal end 75 of the catheter 73 helps avoid any restricted diameter areas along the large lumen 74, and also helps prevent the attachment of the large lumen 74 over the tubular extension 72 from causing a restriction in the diameter of the smaller (irrigation) lumen 76 at the proximal end 75.

A flow channel 77 extends away from the bottom of the second cylindrical opening 71 and is in fluid flow communication with the small lumen 76 of the catheter 73. The flow channel 77 communicates with an L-shaped tubular member 78 which includes a luer-type connection opening 79 designed to receive the flexible fluid vial 64 (shown in FIG. 8). The L-shaped tubular member 78 includes a one-way valve 80 therein preferably formed as a soft tubular sleeve which collapses when pressurized and allows fluid to be injected into the small lumen 76 of the catheter 73 through the flow channel 77, but inhibits fluid flow in the opposite direction.

The catheter sleeve 29, which surrounds the catheter 73, is affixed to the housing 66 by the attachment ring 81, in a friction fit manner, and an air flow path from inside the sleeve 29 through the connector 65 to the atmosphere is formed by the air flow channel 82.

The preferred manner of assembly of the suction catheter device 15 of the present invention is as follows. First, depending on whether a single-lumen or dual-lumen catheter is used, the single-lumen or dual-lumen valve-end connector 49 or 65, respectively, is assembled. In the case of the single-lumen valve-end connector 39, the proximal end of the catheter 31 and the distal end of the septum 52 are bonded into the tubular channel 62 of the snap-in insert 51. The housing 50 is then slid over the sleeve 29 and the distal end of the catheter 31 is inserted through the proximal end of the sleeve 29 and passed completely therethrough. The housing 50 is drawn proximally along the sleeve 29 until the snap-in insert 51 is drawn into the housing 50 past the annular shoulder 54 in the passageway 53 thereof and snapped into position such that the locking shoulder 59 and tapered edge 60 of the fins 58 of the snap-in insert 51 are positioned adjacent the annular shoulder 54 and tapered portion 61 of the channel 53, with the proximal end of the sleeve 29 frictionally held therebetween.

The manifold-end connector 18 is then assembled by first passing the sleeve attachment ring 24 over the distal end 40 of the catheter 31 and over the sleeve 29. Then the magnifying insert 25 is passed over the distal end 40 of the catheter 31 until the distal end 40 extends a predetermined distance beyond the magnifying insert 25. The sleeve 29 is then extended over the magnifying insert 25 and the sleeve attachment ring 24 is pushed onto the cylindrical extension 27 of the magnifying insert 25 to frictionally fit therewith and trap the sleeve 29 therebetween. The remainder of the sleeve 29 extending beyond the distal end of the attachment ring 24 is then folded or rolled back over the attachment ring 24. A sealing ring 35 is then inserted into the annular locking shoulders 33 of the housing 50 and the entire sub-assembly consisting of the magnifying insert 25, the sleeve attachment ring 24, and the portion of the sleeve 29 wrapped around the sleeve attachment ring 24, are then inserted into the housing 19 through the base ring 22 until the annular locking shoulder 34 of the magnifying insert 25 snaps into, and locks behind, the annular locking shoulder 33 of the housing 19 where it presses against the sealing ring 35 in an air-tight manner.

When assembled in this manner, the sleeve 29 is attached to the manifold-end connector 18 such that the catheter 31 can be withdrawn through the connector 18 at least so far as to allow the ring marking 38 thereon to be positioned within the lens 26 of the magnifying insert 25, and to allow the adaptor 20 to protect the distal end 40 of the catheter 31 when the connector 18 is being attached to the manifold 11.

If it is desired to assemble a dual-lumen suction catheter device 15, the valve-end connector 65 thereof (as shown in FIG. 9) must first be assembled by passing the attachment ring 81 thereof over the proximal end 75 of the catheter 73 and the proximal end of the sleeve 29 and then inserting the proximal end 75 of the catheter 73 into the second cylindrical opening 71 until a large lumen 74 thereof is securely attached to the tubular extension 72, (being careful, of course, not to inadvertently block the flow channel 77 by the proximal end 75 of the catheter 73). The catheter 73 can then be permanently affixed within the cylindrical opening 71 by any known means such as by solvent bonding or the like. The proximal end of the sleeve 29 is then wrapped around the attachment ring 81 and the attachment ring 81 is affixed by friction fit to the housing 66. Any part of the sleeve 29 extending beyond the proximal side of the attachment ring 81 can then be trimmed off if desired.

The slitted septum 68 is then forced into the cylindrical opening 67 until it engages with the annular shoulder 69 therein, and the one-way valve 80 is inserted into the L-shaped tubular member 78 which itself is then permanently attached to the housing 66 around the flow channel 77 thereof.

The remaining assembly operations of the dual-lumen version of the suction catheter device 15 of the present invention are identical to the assembly of the single-lumen version described above.

Operation of the suction catheter device 15 within the respiratory support system 10 is preferably as follows. First, the ventilator manifold 11 is attached to the tracheal tube which has previously been inserted into the patient's trachea, and the ventilator circuit of the respiratory support system is attached to the manifold 11 in a well-known manner. The manifold-end connector 18 of the suction catheter device 15 is then inserted into the accessory access port 16 of the manifold 11 and rotated to its above-described locking position therewith. A suction control valve 56 is then inserted into the valve-end connector 49 and attached to a source of suction pressure in a well-known manner.

When it is desired to suction the patient's trachea or lungs, the catheter 31 is advanced through the manifold-end connector 18, the manifold 11, and the tracheal tube into the patient's trachea and lungs any desired distance (which can be monitored by the medical worker performing the procedure by viewing the number markings 39 which appear through the lens 26 of the connector 18). Aspiration of the patient's trachea and lungs is then performed and the catheter 31 is withdrawn until the medical worker can view the ring marking 38 through the lens 26. The medical worker may then clean the distal end of the catheter 31 by injecting fluid through the access port side opening 47 and the injection fluid opening 46 of the adapter 20, and subsequently suctioning the fluid through the catheter 31. Alternatively, a medical worker may inject lavage fluid through the access port side opening 47 into the adapter 20 and allow it to pass into the manifold 11 and down the patient's trachea and lungs, and thereafter insert the catheter 31 into the patient's trachea and lungs to aspirate the patient to remove the lavage fluid.

When it becomes necessary to remove the suction catheter device 15 from the manifold 11, the manifold-end connector 18 is merely detached from the accessory access port 16 and withdrawn therefrom. Alternatively, if it becomes necessary to replace the suction control valve 56, it can be disconnected from the valve-end connector 47 and replaced. In either instance, no loss of PEEP from the manifold 11 occurs due to the normally closed manifold valve 17 of the manifold 11 and/or the slitted septum 52 of the valve-end connector 49.

Use of the alternative embodiment of the suction catheter device 15 which includes the dual-lumen catheter 73 and the dual-lumen valve-end connector 65 is similar to that described above. However it includes the added feature of allowing lavage fluid to be injected into the patient's trachea and/or lungs through the irrigation lumen 76 of the dual-lumen catheter 73. This is done by placing a flexible fluid vial 64 in fluid connection with the luer connector opening 79 of the valve-end connector 65 and injecting fluid through the L-shaped tubular member 78 and the flow channel 77 into the irrigation lumen 76. This method of injecting irrigation fluid for lavage has the added feature of injecting the fluid directly from the distal end of the catheter 73 to allow more directed and forceful fluid flow into the patient's trachea and lungs.

If desired, "time-in-use" markings may be placed on the manifold 11, the suction catheter device 15, and/or the suction control valve 56 to provide the medical worker with an indication of the amount of time the particular component has been part of the respiratory support system. Further, if desired, the "time-in-use" markings may indicate a recommended time period for use, and further if desired, may include means for indicating of the amount of time which has passed since the component has been assembled within the respiratory support system. An example of such means is a color change indicator which can be actuated when the component is attached to the respiratory support system and will change colors at a predetermined time period to signal the medical worker that the component is due to be changed out of the respiratory support system. Other indicators may be used, such as marking areas, tags, etc. may also be used and remain within the spirit and scope of the present invention.

It should be understood from the foregoing that, while particular embodiments of the invention have been illustrated and described, various modifications can be made thereto without departing from the spirit and scope of the invention. Therefore, it is not intended that the invention be limited by the specification; instead, the scope of the present invention is intended to be limited only by the appended claims.

We claim:

1. A suction catheter device for use with a respiratory support system including a ventilator and a suction source, said device comprising:

a catheter having a proximal end and a distal end;

a distal end connector slidably attached to said catheter for connecting said catheter device to a ventilator of a respiratory support system;

a proximal end connector fixedly attached to said proximal end of said catheter for connecting said suction catheter device to a suction source; and said proximal end connection including a normally closed valve for preventing fluid flow through said catheter when said proximal end connector is not attached to a suction source, and for allowing fluid flow through said catheter when said proximal end connector is attached to a suction source, said normally closed valve automatically being placed in an open position responsive to said proximal end connector being engaged to a suction source.

2. A suction catheter device according to claim 1 wherein said distal end connector includes a lens for viewing said catheter therethrough.

3. A suction catheter device according to claim 2 wherein said lens is a magnifying lens.

4. A suction catheter device according to claim 3 wherein said catheter further includes markings thereon,
   whereby, sliding movement of said catheter through said distal end connector causes said markings to be viewable through said magnifying lens.

5. A suction catheter device according to claim 4 wherein said markings include at least one marking for indicating a completely withdrawn position of said catheter within said distal end connector,
   whereby, when said at least one marking is viewable through said magnifying lens, said catheter is located at its completely withdrawn position.

6. A suction catheter device according to claim 4 wherein said markings include a series of uniformly spaced markings positioned along said catheter at a predetermined distance from said distal end thereof, whereby, positioning of any one of said series of markings to be viewable through said magnifying lens also positions said distal end of said catheter a predetermined distance away from said distal end connector.

7. A suction catheter device according to claim 1 wherein said distal end connector further includes a seal through which said catheter passes.

8. A suction catheter device according to claim 7 wherein said magnifying lens abuts said seal in air-tight relationship.

9. A suction catheter device according to claim 8 wherein said distal end connector includes a lock for attaching said distal end connector to a ventilator in a single unique relative orientation.

10. A suction catheter device according to claim 1 wherein said catheter distal end includes a plurality of openings formed therein.

11. A suction catheter device according to claim 1 wherein said normally closed valve is a slitted septum.

12. A suction catheter device according to claim 1 wherein said proximal end connector forms an air flow passage therethrough which allows passage of air through said proximal end connector independent of said normally closed valve for preventing fluid flow through said catheter.

13. A suction catheter device according to claim 12 further including a sleeve attached to said distal end connector and said proximal end connector and enveloping the portion of said catheter located between said distal end connector and said proximal end connector.

14. A suction catheter device according to claim 13 wherein said air flow path allows passage of air within said sleeve through said proximal end connector.

15. A suction catheter device according to claim 1 wherein said catheter is a dual lumen catheter and said proximal end connector includes a tubular member for injecting fluid therethrough into a second lumen of said dual lumen catheter.

16. A suction catheter device according to claim 15 wherein said tubular member for injecting fluid into said dual lumen catheter includes a one-way check valve.

17. A suction catheter device according to claim 16 wherein said one-way check valve includes a collapsible sleeve member.

18. A method of assembling a suction catheter device including the steps of:

fixedly attaching an insert portion of a proximal end connector to a proximal end of a catheter, fixedly attaching a normally closed valve to the insert portion of the proximal end connector which closes the catheter against fluid flow therethrough when in its normally closed condition, inserting the catheter into an elongate sleeve, connecting the insert portion of the proximal end connector to a housing portion of the proximal end connector and to the sleeve, and fixedly attaching a distal end connector to the sleeve to allow for sliding movement of the catheter through the distal end connector by;

passing a sleeve attachment ring over the distal end of the sleeve, passing a magnifying insert over the distal end of the catheter, measuring the length of the catheter to a predetermined distance from the distal end of the magnifying insert, attaching the sleeve attachment ring to the magnifying insert such that the sleeve is frictionally engaged therebetween, wrapping the sleeve around the sleeve attachment ring, and inserting the magnifying insert into a housing portion of the distal end connector to connect the magnifying insert with the housing portion such that the magnifying insert abuts the sealing ring and the sleeve is also frictionally engaged between the sleeve attachment ring and the distal end connector housing.

19. A method according to claim 18 further including bonding the normally closed valve to the insert portion of the proximal end connector means.

20. A method according to claim 18 wherein the housing portion of the distal end connector means includes a window formed therein and the step of inserting the magnifying insert into the housing portion includes positioning a magnifying lens of the magnifying insert within the window.

21. A method according to claim 18 further including the step of placing position indicative markings on the catheter which can be viewed through the magnifying lens of the magnifying insert.

22. A method of assembling a dual lumen suction catheter device including the steps of;

passing an attachment ring over a proximal end of the catheter and the proximal end of an elongate sleeve, inserting the proximal end of the catheter into a cylindrical opening in a proximal end connector housing and securing the proximal end of the large lumen of the catheter in fluid flow connection with a first passage through the proximal end connector housing and securing the proximal end of the small lumen of the catheter in fluid flow connection with a second passage through the proximal end connector housing, affixing a normally closed valve within the proximal end connector housing, fixedly attaching a distal end connector to the sleeve to allow for sliding movement of the catheter through the distal end connector by;

passing a sleeve attachment ring over the distal end of the sleeve, passing a magnifying insert over the distal end of the catheter, measuring the length of the catheter to a predetermined distance from the distal end of the magnifying insert, attaching the sleeve attachment ring to the magnifying insert such that the sleeve is frictionally engaged therebetween, wrapping the sleeve around the sleeve attachment ring, and inserting the magnifying insert into a housing portion of the distal end connector to connect the magnifying insert with the housing portion such that the magnifying insert abuts the sealing ring and the sleeve is also frictionally engaged between the sleeve attachment ring and the distal end connector housing.

23. A method according to claim 22 further including inserting the normally closed valve over the first passage through the proximal end connector housing and placing a one-way check valve in the second passage through the proximal end connector housing.

* * * * *